US011160588B2

(12) United States Patent
Haaja et al.

(10) Patent No.: US 11,160,588 B2
(45) Date of Patent: Nov. 2, 2021

(54) SYSTEM FOR STABILIZING OR LENGTHENING BONE

(71) Applicant: SYNOSTE OY, Espoo (FI)

(72) Inventors: Juha Haaja, Kauniainen (FI); Harri Hallila, Helsinki (FI); Antti Ritvanen, Helsinki (FI); Ryan Livingston, Williston, VT (US); Taneli Kari, Helsinki (FI)

(73) Assignee: Bala Sundararajan, Audubon, PA (US)

( * ) Notice: Subject to any disclaimer, the term of this patent is extended or adjusted under 35 U.S.C. 154(b) by 31 days.

(21) Appl. No.: 16/304,332

(22) PCT Filed: May 4, 2017

(86) PCT No.: PCT/FI2017/050344
§ 371 (c)(1),
(2) Date: Nov. 26, 2018

(87) PCT Pub. No.: WO2017/203097
PCT Pub. Date: Nov. 30, 2017

(65) Prior Publication Data
US 2019/0133650 A1    May 9, 2019

(30) Foreign Application Priority Data

May 27, 2016 (FI) ..................................... 20165445
May 4, 2017 (WO) ................. PCT/FI2017/050344

(51) Int. Cl.
*A61B 17/72* (2006.01)
*A61B 17/66* (2006.01)
(Continued)

(52) U.S. Cl.
CPC .......... *A61B 17/7216* (2013.01); *A61B 17/66* (2013.01); *A61B 17/8004* (2013.01); *A61B 17/7233* (2013.01); *A61B 2090/061* (2016.02)

(58) Field of Classification Search
CPC . A61B 17/7216; A61B 17/7233; A61B 17/66; A61B 17/64; A61B 17/6408; A61B 17/6466; A61B 17/6475; A61B 2090/0641
See application file for complete search history.

(56) References Cited

U.S. PATENT DOCUMENTS 5,263,955 A   11/1993  Baumgart et al.
5,415,660 A    5/1995  Campbell et al.
(Continued)

FOREIGN PATENT DOCUMENTS

CN   102271601 A   12/2011
CN   105476701 A    4/2016
(Continued)

OTHER PUBLICATIONS

Paley D et al.: "Femoral Lengthening over an Intramedullary Nail", Journal of Bone and Joint Surgery, American vol. Journal of Bone and Joint Surgery, US, vol. 79-A, No. 10, Oct. 1, 1997 (pp. 1464-1480), XP-000722086.
(Continued)

*Primary Examiner* — Ellen C Hammond

(57) ABSTRACT

The present invention is about an intra-corporal telescopic osteodistraction device 1 for locking the length of the bone 3 and for providing axial, torsional and bending stability; an extra-corporal force producing device 4a, 4b for producing a force for extension causing a lengthening of the intra-corporal device 1 and the bone 3; a method for bone lengthening and a bone lengthening arrangement utilizing the devices 1 and 4a, 4b of the invention.

6 Claims, 2 Drawing Sheets

Figure 1:
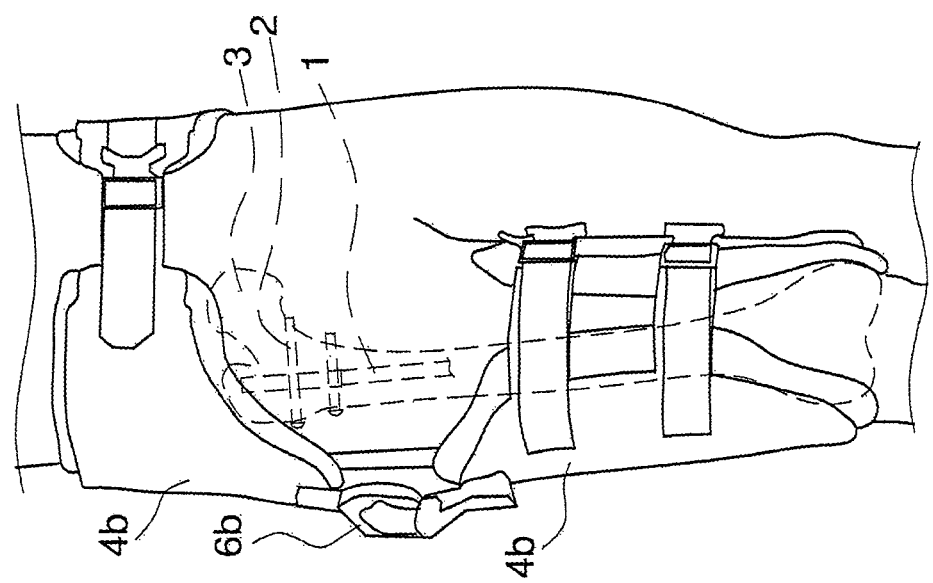

(51) Int. Cl.
*A61B 17/80* (2006.01)
*A61B 90/00* (2016.01)

(56) References Cited

U.S. PATENT DOCUMENTS

| | | | |
|---|---|---|---|
| 5,704,938 A | 1/1998 | Staehlin et al. | |
| 5,704,939 A | 1/1998 | Justin | |
| 5,961,553 A | 10/1999 | Coty et al. | |
| 6,245,075 B1 | 6/2001 | Betz et al. | |
| 2004/0138663 A1* | 7/2004 | Kosashvili | A61B 17/7216 606/62 |
| 2007/0010814 A1 | 1/2007 | Stauch | |
| 2009/0275984 A1 | 11/2009 | Kim et al. | |
| 2011/0196371 A1 | 8/2011 | Forsell | |
| 2011/0230883 A1* | 9/2011 | Zahrly | A61B 17/7216 606/63 |
| 2012/0296234 A1 | 11/2012 | Wilhelm et al. | |
| 2014/0250674 A1 | 9/2014 | Pool et al. | |

FOREIGN PATENT DOCUMENTS

| | | |
|---|---|---|
| DE | 198 29 523 A1 | 1/2000 |
| EP | 0 639 352 A1 | 2/1995 |
| EP | 2 151 208 A2 | 2/2010 |
| JP | 2004526544 A | 9/2004 |
| JP | 2012507340 A | 3/2012 |
| WO | 01/24697 A1 | 4/2001 |
| WO | 2011/148047 A1 | 12/2011 |
| WO | 2013/176632 A1 | 11/2013 |

OTHER PUBLICATIONS

Finnish Patent and Registration Office Search Report (U.S. Appl. No. 20/165,445) (3 pages—dated May 12, 2016).

* cited by examiner

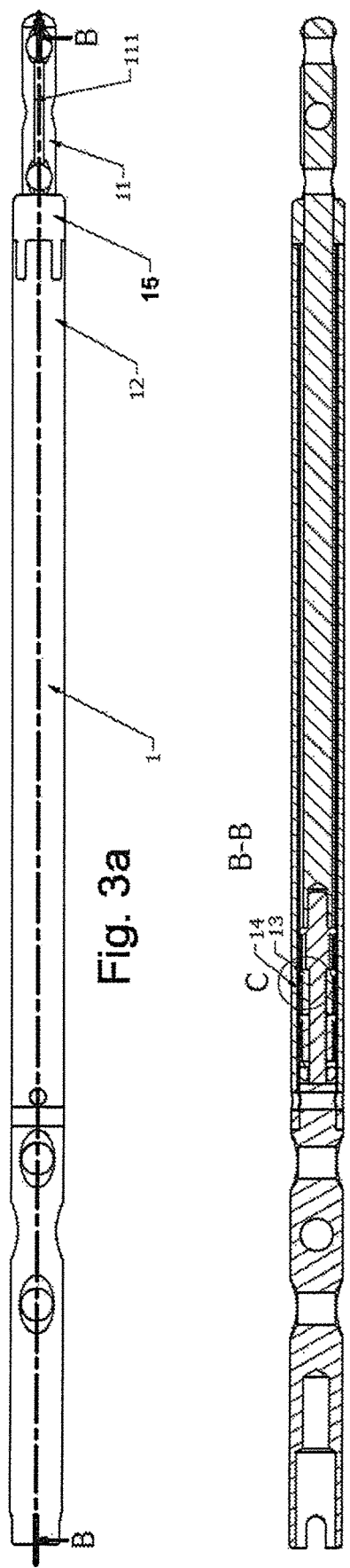
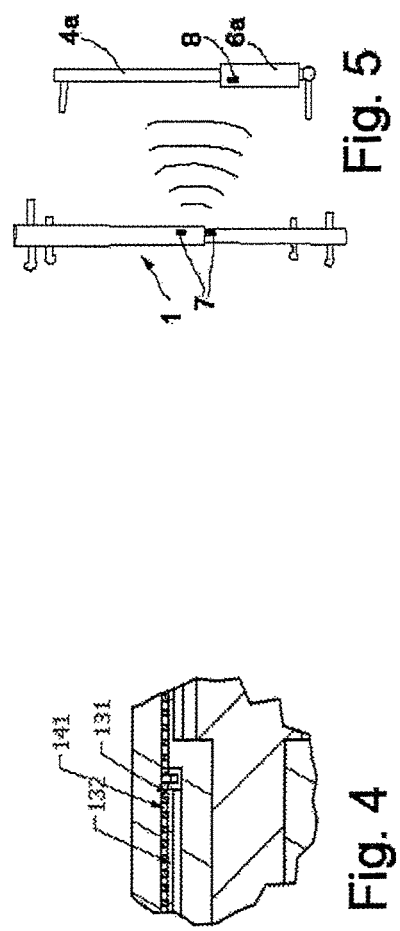

SYSTEM FOR STABILIZING OR LENGTHENING BONE

The invention relates to bone lengthening and gradual skeletal deformity correction. Especially it relates to bone lengthening in a convenient and low cost manner.

The bone lengthening and gradual skeletal deformity correction techniques are routinely applied in at least the following treatments: bilateral and unilateral lengthening of femur and tibia, stump lengthening of femur, tibia, humerus and fingers, gradual correction of ankle via talus and calcaneus osteotomies, adaptive rodding for progressive congenital, neuromuscular, idiopathic or syndromic scoliosis, metatarsal and metacarpal lengthening, gradual correction of craniomaxillofadal deformity, and gradual correction of lower limb deformity by opening wedge osteotomies (e.g. High Tibial Osteotomy).

It is known from prior art external fixators for bone lengthening. Their advantages are low costs and accessibility. However, the treatment is typically painful and inconvenient for the patient.

Further problems of the external fixators to mention are at least infection rates, duration of rehabilitation, highly obtrusive and inconvenient devices attached to the patient, disturbing patients sleep, wounds and their management, possible broken or infected pins and changing them, poor cosmetic outcome, need of special clothing, and disturbing physiotherapy.

A traditional ring frame for limb lengthening is typically called an Ilizarov Frame after its inventor.

Further, intramedullary implants for bone lengthening are known. They are more convenient and cause less complications to the patients. However, they are typically very expensive and the accessibility is low.

Further problems of the intramedullary implants to mention are at least availability only in certain markets, only partial weight bearing and not allowing physiotherapy in full extent, demanding surgery, not available for all patient groups, indirect measurement of the lengthening, high amount of technical issues and no possibility for implant maintenance in the case of jamming, breakages and uncontrollability, incompatible with magnetic resonance imaging (MRI), and products are highly regulated.

Looking at the disadvantages of the prior art, there is clear need for a hybrid. solution, which would be more convenient and causing less complications to the patient, but at the same time being accessible and inexpensive.

Further in the prior art is one hybrid-kind solution with an implantable intramedullary nail and an external fixator. As this so called Lengthening Over Nail (LON)-approach requires two surgeries (implantation of the intramedullary nail and separate surgery for fixing distal locking screws after lengthening), there is high risk of severe infections. The implantable parts of the solution do not provide torsional stability or axial stability in lengthening.

In addition to the LON requiring additional surgery in an operating room to insert the distal screws when lengthening is complete, it also requires reaming the medullary canal by the length of the intended lengthening distance and the minimum distance for the distal screw fixation and provides low biomechanical stability at the distal fragment of the bone after lengthening.

Some further hybrid-kind solutions are known in prior art. These are called Lengthening And Then Nailing (LATN), Lengthening Over Plate (LOP) and Lengthening And Then Plating (LATP).

The LATN requires invasive and infection prone insertion surgery to insert the intramedullary nail after the lengthening has been completed, it requires several extra safety measures to prevent the usually infected pin tracts from infecting the surrounding tissue of the intramedullary nail to be inserted. Further, in LATN the placement of the external frame is very demanding as the intramedullary nail to be inserted in the future needs to be taken into account without the nail in place as reference and for navigation.

The LOP requires a second surgery in an operating room to insert the distal screws to stabilize the plate. Unstable fractures are always biomechanically less stable when fixated with a plate than intramedullary nails.

The LATP requires invasive and infection prone insertion surgery to insert the plate after the lengthening has been completed, it requires several extra safety measures to prevent the usually infected pin tracts from infecting the plate to be inserted. As above, the unstable fractures, which is the case in distraction osteogenesis, are always biomechanically less stable when fixated with a plate than with intramedullary nails.

It is previously known from publications EP 0 639 352 A1, WO 01/24697 A1, US 2009/275984 A1, DE 198 29 523 A1 and EP 2 151 208 A2 intra-corporal telescopic osteodistraction devices and extra-corporal force producing devices.

The aim of the present invention is to provide a solution for bone lengthening, wherein the treatment would be more convenient and causing less complications to the patient, but at the same time being accessible and inexpensive. Further, the aim of the invention is to provide a solution, wherein only one surgery is needed and there is torsional stability and axial stability in lengthening. Further, the aim of the invention is to provide better controllability than with the intramedullary implants and allow maintenance of the lengthening force producing means or device during the treatment.

The aim of the invention is achieved by the intra-corporal telescopic osteodistraction device of claim 1, the extra-corporal force producing device of claim 8, the method for bone lengthening of claim 10 and the bone lengthening arrangement of claim 12. The preferred embodiments of the invention are introduced in further claims.

The intra-corporal telescopic osteodistraction device of the invention includes two fixing points for attachment to a bone in a way that enables increasing the distance between the fixing points in a controlled manner, and has means allowing unidirectional movement in the direction increasing a distance between the fixing points and preventing movement in the return direction and preventing twisting of the device and the bone. The device of the invention is characterized in that the lengthening movement of the bone is arranged by an extra-corporal force producing device, which is in connection to the bone to be lengthened, wherein the osteodistraction device is arranged to lengthen with the lengthening movement of the bone in unidirectional way.

The device connection to the bone may be realized by a direct attachment to the bone by pins, wires screws, extra-cortical clamps or similar. Alternatively, the connection may be realized by attachment to the physical or anatomical features, which further are connected to the bone, or other way cause the movement and lengthening of the bone.

The means allowing unidirectional movement, preventing movement in the return direction and preventing undesirable twisting and bending of the device may be provided integrally within one and the same single entity. Alternatively, the means may constitute of more physical entities. In a typical embodiment, the entity for preventing the twisting may constitute of separate physical bodies than the entity allowing unidirectional movement in the direction increasing a distance between the fixing points and preventing movement in the return direction.

In this context, the undesirable twisting means unintentional non-free rotation of a rod, telescopic tubes, bone, bone segments or similar over their longitudinal axis.

According to an embodiment of the invention, the intra-corporal telescopic osteodistraction device may have means indicating the amount of its lengthening. Further, the indication means may produce an audible signal or the indication means comprise means for producing an RF-signal.

Alternatively, the indication means may comprise means for producing a change in a sensible static or permanent magnetic field.

According to another embodiment of the invention, the intra-corporal telescopic osteodistraction device is implantable in or on the bone.

In the intra-corporal telescopic osteodistraction device the said way that enables increasing the distance between the fixing points may also enable decreasing the said distance i.e. retraction.

The wanted retraction and decreasing of the distance may be achieved by e.g. slotted screw holes, dynamization of the fixing points, by using bi-functional or other springs, releasing an internal lock by magnets, or other means of external energy, screw removal, discrete ratchet mechanism with larger tooth length than the intended lengthening step, change of the screw configuration around the fixing points and/or separate retraction part of the implant.

According to the invention, an extended position following the device lengthening with the lengthening movement of the bone may be held and/or locked by implant ratchet mechanisms or other means allowing unidirectional movement.

The extra-corporal force producing device of the invention arranges the lengthening of a bone having the intra-corporal telescopic osteodistraction device implanted in or on the bone.

It is still another embodiment of the invention, wherein the extra-corporal force producing device may have means for receiving the indication of the amount of the lengthening of the intra-corporal telescopic osteodistraction device. Further, the information of the indication of the amount of the lengthening of the intra-corporal telescopic osteodistraction device may be used for controlling the lengthening of the bone.

Further, the extra-corporal force producing device may be fixed to the bone fragments by means of wires, pins, half-pins or extra-cortical clamps. Alternatively, the extra-corporal force producing device may be entirely outside the body without any percutaneous parts.

In the method for bone lengthening, according to the invention, the intra-corporal telescopic osteodistraction device is implanted in or on the bone; and the following steps are repetitively executed:
the extra-corporal force producing device is connected to the bone to be lengthened;
the distance between the fixing points of the intra-corporal telescopic osteodistraction device is increased by the extra-corporal force producing device;
the extra-corporal force producing device is disconnected of the bone.

The method is characterized in, that during each repetitive step, the means of the intra-corporal telescopic osteodistraction device lock the length of the intra-corporal telescopic osteodistraction device and the bone.

The same results for bone lengthening may be achieved by not disconnecting and connecting the external device between the steps of increasing the distance between the fixing points. However, if not detached, the maximum comfort for the patient may not be achieved, as the external device has to be carried along all the time.

Further, in the method for bone lengthening of the invention, as the desired lengthening of the bone is reached, the intra-corporal telescopic osteodistraction device is removed.

The bone lengthening arrangement of the invention comprise an intra-corporal device for locking the length of the bone and for providing axial, torsional and bending stability, an extra-corporal device for producing a force for extension causing a lengthening of the intra-corporal device and the bone, means for detecting and transmitting information about the lengthening of the intra-corporal device, and means for receiving the information about the lengthening and for controlling the extension in the extra-corporal device.

Further, in the arrangement of the invention the said intra-corporal device is implanted in or on the bone, and the said extra-corporal device is connected to the bone or to the limb of the bone only when there is need for lengthening.

In the method of the invention, the conventional Lengthening Over Nail-treatment is improved by replacing the implantable nail of fixed length by an extending implant with a telescope mechanism. To achieve a more inexpensive solution for emerging markets, only the smart locking mechanism of known telescopic intramedullary implants is used without any need for wireless energy transfer and implantable elements that produce force or torque. For the force production, to achieve the lengthening, external devices are used. In addition to external force production and implemented locking mechanism, it is advantageous to transfer the information about the implant lengthening to the system for further control of the lengthening.

The usage of the robust implant minimizes the number of needed pins in fixation of the external device. In addition, due to the usage of modern telecommunication or audio-based information transfer or sensing of changes in a static magnetic field, neither does the information transfer to the force production for lengthening necessitate any physical connections between the devices. As a result, the present contribution helps in every aspect to minimize invasiveness of the external device by allowing more flexible fixation with fewer or no pins, which maximizes the patient comfort.

To control the lengthening, the implantable part of the arrangement of the invention may transmit signals containing the lengthening information. Based on this information, the lengthening of the external part is controlled, and as a result, the bone lengthening is controlled.

There are several ways to realize the lengthening detection and control. The signal generation may simply base on generation of audible signal caused by mechanical locking of the mechanism or by a separate ratchet. Alternative possibilities can be e.g. RFID tags, which may be included in both parts of the telescopic nail and thus detecting the distance between the tags. Similar constructions can be built with intelligent materials. The lengthening information may further be transmitted to external device e.g. In form of radio or audible signals. Further, the change in the static magnetic field may be measured. Alternatively, any implantable electronic components, such as strain gauge, or resistive, capacitive or inductive position or displacement sensors, may be utilized.

In one preferred embodiment of the invention, the intramedullary nail has the telescopic mechanism as set forth in publication WO 2011/148047 A1 with the locking function of the wedge means. In this kind of hybrid approach of the invention, the torsional and axial stability is achieved by the nail. Therefore, the external fixator does not need to serve for the stability anymore. Therefore, the external part of the fixator could be simplified to be less invasive by using fewer or no pins or wires. One embodiment would have only two pins that are fixed to the bone and detached from the external part of the fixator if required. Further it may be possible to formulate a wearable device externally lengthening the bone without any percutaneous connection to the bone or the intramedullary telescopic nail.

Further, the external device may include means for receiving data from the intramedullary telescope about the lengthening. Alternatively, the data may be collected by a separate device.

Figure 2:
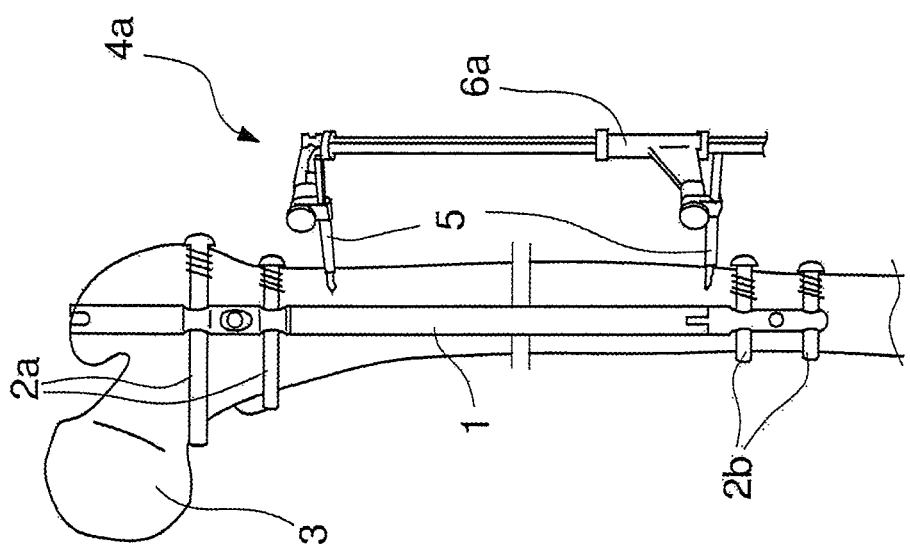

The embodiments of the invention are described in more detail by referring to the attached drawings, wherein:

FIG. 1 describes a first embodiment of the invention, including the telescopic implantable device and an external device;

FIG. 2 describes a second embodiment of the invention, including the telescopic implantable device and an external device;

FIG. 3a describes an embodiment of the implantable device according to the invention;

FIG. 3b shows the cross-section of the embodiment of FIG. 3a;

FIG. 4 describes a detail C of the FIG. 3b;

FIG. 5 describes the lengthening information transfer in the arrangement of the invention.

The FIG. 1 shows a preferred embodiment of the invention. The telescopic implantable device 1 is fixed to a bone 3. The bone 3 has been cut into at least two sections by an osteotomy. In its fixing point the device 1 is fixed to the bone 3 using at least one locking screw 2a, 2b at each end. Typically, one to three screws are used proximally and distally. An external device 4a is fixed to the bone fragments by means of pins 5, half-pins or extra-cortical clamps. The external device 4a comprises means 6a for extending the external device 4a.

The FIG. 2 shows another preferred embodiment of the invention. The telescopic implantable device 1 is fixed to a bone 3 cut by osteotomy. The external device 4b is realized non-invasively by a design attaching to the anatomical outer features of the body. In one preferred embodiment, the external device is attached on patients anatomical features, e.g. knee, waist or ankle. The external device 4b is extended periodically by means 6b and thus achieving the desired daily lengthening target required by the distraction osteogenesis treatment.

The telescopic nail or telescopic implantable device of the invention lengthens as the two fixing points are separated by pulling or drawing.

The means 6a or 6b for lengthening the external device 4a or 4b may include screws. Screws may e.g. be manually adjusted to lengthen the external device 4a or 4b. Alternatively, the means 6a or 6b may include an electric motor or other form of linear actuator for extension.

The FIGS. 3a and 3b show the structure of the implant 1 including two sections 11 and 12. The extension of the external device 4a, 4b causes the sections 11 and 12 to slide in relation to each other. The new extended position of the implant 1 is held and/or locked by the implant ratchet mechanisms 13 engaging into the features of the implant structure 14, or other means allowing unidirectional movement such as linear one-way clutches comprising balls, roller or sprags. These features can be realized directly to the outer structure 12 of the implant by means of matching for example rifling. The features can also be realized as a separate insert that is attached to the implant outer structure 12. This can be done e.g. as a slotted tube prepared e.g. by laser cutting or electric discharge machining.

The FIG. 4 shows a ratchet mechanism. The marked portion C of FIG. 3b scaled in 6:1 clarifies the details of a preferred embodiment for the mechanism. The alternative mechanisms and details are disclosed e.g. in publication WO 2011/148047 A1.

The teeth 131 engage to the slots 141 in the implant structure. The extension force is applied to the arm 132 of the ratchet mechanism 13 by the extension of the external device 4a, 4b. The ratchet teeth 131 disengages from the slot 141 and is able to move into a new slot 141. By this, the extension of the implant is achieved. The amount of the ratchet mechanisms 13 and the ratchet teeth 131 can vary depending on application area and device size. The larger the number of ratchet mechanisms 13 and ratchet teeth 131 the better the load bearing capacity of the device. The ratchet mechanism 13 engage in the slotted tube in a discrete manner with defined intervals. The interval, or step size, can be changed changing the resolution of the slot features 141. All of the ratchet teeth 131 do not need to engage simultaneously. The teeth 131 or slots 141 can be manufactured in an offset pattern that allows higher resolution, or smaller step size, to be realized when different teeth 131 lock into the features on successive lengthenings.

The ratchet teeth 131 and ratchet aria 132 can also be designed in a manner that when engaging into the slots 141 an audible signal occurs. This audible signal can be sensed and/or detected by the external device 4a, 4b by, means of e.g. high precision microphone. The information of the audible signal can be utilized to contra the lengthening speed.

Additionally, a tension string can be placed inside the implant. The tension string is allowed to slide and lengthen when the implant is being lengthened. As the external device sends a spectrum of sound signals to the implant via speaker, the string is placed into resonant vibration creating an audible signal at a distinct frequency. The external device can detect the frequency by means of a precision microphone and thus detect the length of the string and the implant.

Alternatively, the audible signal may be detected by means of a typical stethoscope, and the external device may be adjusted manually based on this information.

The ratchet mechanisms 13 in combination with the implant structure 14 can be designed to provide axial, torsional and bending stability to the treated bone 3. The torsional stability of the implant that prevents the unwanted twisting during the lengthening treatment can be further improved by using a key lock ring 15 that engages to grooves 111 in the telescoping implant portion 11. As the fixation stability is provided by the implant, the external device 4a, 4b can be removed even between the successive lengthening sessions. This provides the patient increased comfort, as the frame of the external device has to be attached to the bone and/or limb only for a limited time.

The FIG. 5 shows one embodiment for transferring the lengthening information from the intra-corporal device to the extra-corporal device. The means 7 on the lengthening part of the intra-corporal device 1 detect and transfer the lengthening information as an audible or a radio signal and the means 8 on the adjustment part of the extra-corporal device (4a, 4b) receive the information.

The meaning of the external device is to lengthen the bone and internal device. As it is not supposed to support the bone and/or fraction, it is possible to remove the fixator also during the lengthening treatment.

By the solution of the invention, a novel bone distraction treatment is achieved. As the number of connection pins outside the body is reduced or eliminated, the infection rates as well as the pain of the patient are reduced. As there is no continuous need for the outer frame, the rehabilitation is improved and accelerated. With detachable pins, the needed devices may be unobtrusive, this removes the need of special clothing and the patients sleep is not unnecessarily disturbed. With less pins, there is less need of wound management, less pin site infections, less pin breakages and better cosmetic outcome. As no force producing elements inside the implant is required, there is more space for the mechanism and greater material thickness can be used; it may be possible to provide a full weight bearing, with no disturbance on physiotherapy or patient's normal daily activities. With simplified telescopic intramedullary nail, the treatment is more available in the sense of costs and size and shape. Also due to the greater material thicknesses more cost effective materials may be selected. Direct measurement of lengthening is advantage on the controllability. With possibility to easily maintain the external force producing parts, less jamming and breakages happen. As there is no need for magnets or other incompatible structures or materials, the MRI is also applicable. The necessary products would be less regulated because the implantable parts can be manufactured entirely from single well established biocompatible material and no hazardous active elements inside the implant are necessary. Installation needs only one surgery, but the lengthening and consolidation of the bone is still stable, with lower risks of severe infections.

According the present invention, the lengthening arrangement has both the proximal and distal screws in place after insertion surgery, and removal of the external fixator is significantly smaller operation with lower cost and infection rate than inserting an implant or a screw as in the LON, LOP, LATN or LATP. It requires only one surgery in an operating room and if a percutaneous external fixator was used then the significantly smaller external fixator removal operation. Reaming of only the distance of the distal screw fixation is required, which makes the treatment and operations significantly less invasive compared to the LON technique. It provides significantly higher stability after lengthening due to longer overlapping lengths of the bone and the nail compared to any other hybrid-kind solutions. As the placement of the external fixator is made after the inserting the intramedullary nail, the insertion is safer and easier than in the known technologies. The intramedullary nail provides better stability leading to lower risk of device breakage and higher load bearing capability.

The invention claimed is:

1. A system for stabilizing bone comprising:
    an intra-corporal telescopic osteodistraction device, including two fixing points for attachment with locking screws to a bone in a way that enables increasing the distance between the locking screws in a controlled manner, wherein the device is configured to provide unidirectional movement in the direction increasing a distance between the fixing points and preventing movement in the return direction and preventing twisting of the device and the bone, wherein the osteodistraction device is arranged to lengthen with the lengthening unidirectional movement of the bone, and configured to indicate the amount of lengthening; and
    an extra-corporal device configured to produce a force for extension causing the lengthening of the intra-corporal device and the bone;
    wherein the extra-corporal device is adapted to be attached to outer features of the bone and includes at least two screws and configured to be manually adjusted to lengthen the extra-corporal device.

2. The system of claim 1, wherein an audible signal is provided to indicate the amount of lengthening of the intra-corporal telescopic osteodistraction device.

3. The system of claim 1, wherein an RF-signal is provided to indicate the amount of lengthening of the intra-corporal telescopic osteodistraction device.

4. The system of claim 1, wherein the intra-corporal telescopic osteodistraction device is implantable in the bone.

5. The system of claim 1, wherein in an extended position following the intra-corporal telescopic osteodistraction device lengthening with the lengthening movement of the bone, the extended position is held and/or locked.

6. A system for lengthening bone, comprising:
    an extendable intra-corporal device configured to extend the bone and locking the length of the bone and configured to provide axial, torsional and bending stability; and
    an extra-corporal device configured to produce a force for extension causing a lengthening of the intra-corporal device and the bone;
    wherein the system detects and transmits information about the lengthening of the intra-corporal device; and
    receives the information about the lengthening and for controlling the extension in the extra-corporal device
    wherein the extra-corporal device is adapted to be attached to outer features of the bone and includes at least two screws and is configured to be manually adjusted to lengthen the extra-corporal device.

* * * * *